(12) United States Patent
Sangha (10) Patent No.: US 8,740,812 B2
(45) Date of Patent: Jun. 3, 2014

(54) LOW PRESSURE SAMPLE COLLECTION APPARATUS

(75) Inventor: Jangbir S. Sangha, Overland Park, KS (US)

(73) Assignee: The Bode Technology Group, Inc., Lorton, VA (US)

(*) Notice: Subject to any disclaimer, the term of this patent is extended or adjusted under 35 U.S.C. 154(b) by 1315 days.

(21) Appl. No.: 11/787,313

(22) Filed: Apr. 16, 2007

(65) Prior Publication Data

US 2007/0255175 A1  Nov. 1, 2007

Related U.S. Application Data

(60) Provisional application No. 60/792,057, filed on Apr. 14, 2006.

(51) Int. Cl.
| | |
|---|---|
| *A61B 10/00* | (2006.01) |
| *A61B 5/00* | (2006.01) |
| *B65D 81/00* | (2006.01) |
| *A61B 19/02* | (2006.01) |
| *A61B 19/00* | (2006.01) |
| *A61F 13/38* | (2006.01) |
| *A61B 10/02* | (2006.01) |
| *B01L 3/00* | (2006.01) |
| *G01N 1/02* | (2006.01) |

(52) U.S. Cl.
CPC ............ *A61B 10/02* (2013.01); *A61B 10/0096* (2013.01); *A61B 2019/0274* (2013.01); *A61B 2019/446* (2013.01); *A61F 13/38* (2013.01); *A61B 2019/442* (2013.01); *A61B 10/0283* (2013.01); *B01L 3/5029* (2013.01); *G01N 2001/028* (2013.01); *A61B 10/0045* (2013.01); *A61B 2019/0273* (2013.01)

USPC ............................ 600/572; 600/569; 600/573

(58) Field of Classification Search
CPC ........... A61B 10/0045; A61B 10/0051; A61B 10/0064; A61B 10/0096; A61B 10/0291; A61F 13/15
USPC ......... 600/562, 563, 564, 565, 566, 567, 568, 600/569, 570, 571, 572
See application file for complete search history.

(56) References Cited

U.S. PATENT DOCUMENTS

| | | | | | |
|---|---|---|---|---|---|
| 2,835,246 | A | * | 5/1958 | Boettger | 600/570 |
| 3,674,007 | A | * | 7/1972 | Freis | 600/572 |
| 4,175,008 | A | * | 11/1979 | White | 600/572 |
| 5,129,402 | A | * | 7/1992 | Koll et al. | 600/572 |
| 5,151,094 | A | * | 9/1992 | Hanifl | 604/118 |
| 5,921,972 | A | * | 7/1999 | Skow | 604/313 |
| 6,312,395 | B1 | * | 11/2001 | Tripp et al. | 600/572 |

(Continued)

*Primary Examiner* — Adam Eiseman
(74) *Attorney, Agent, or Firm* — Polsinelli PC (57) ABSTRACT

A low pressure sample collection apparatus includes a double-ended cap member having similarly sized plug members extending from opposite sides, a vacuum connection nipple on one side and a shaft connection portion one the opposite, a passage extending through the cap from the nipple to the shaft connection portion, a tubular shaft connected to the shaft connection portion and having a sample collection swab member secured to an outer end thereof, and a container member having one end closed and an opposite end open. The cap member is reversibly plugged into the container either to use the container as a handle or to position the swab within the container for protection. A vacuum source may be connected to the assembly to draw air through the swab. The shaft may have a barrel telescoped thereon for separation of the swab from the shaft without contacting the swab.

25 Claims, 7 Drawing Sheets

(56) References Cited

U.S. PATENT DOCUMENTS

| | | | |
|---|---|---|---|
| 6,350,415 B1* | 2/2002 | Niermann et al. | 422/103 |
| 7,452,714 B2* | 11/2008 | Eversdijk | 435/309.1 |
| 2005/0010132 A1* | 1/2005 | Pestes et al. | 600/572 |
| 2005/0252820 A1* | 11/2005 | Sanchez-Felix et al. | 206/569 |
| 2006/0192098 A1* | 8/2006 | Danylewych-May | 250/281 |

* cited by examiner

LOW PRESSURE SAMPLE COLLECTION APPARATUS

CROSS-REFERENCE TO RELATED APPLICATION

This application claims priority under 35 U.S.C. 119(e) and 37 C.F.R. 1.78(a)(4) based upon copending U.S. Provisional Application Ser. No. 60/792,057 for LOW PRESSURE COLLECTION APPARATUS, filed Apr. 14, 2006, which is incorporated herein by reference.

BACKGROUND OF THE INVENTION

The present invention relates to the collection of material samples, as for forensic, scientific, or diagnostic purposes, and more particularly, to devices for collecting such samples and preserving them from contamination prior to laboratory analysis.

Crime scene evidence is collected to establish facts related to a crime or a suspected crime and for identification and/or elimination of suspects and may be presented at a trial for the determination of guilt or innocence of accused individuals. Often, the evidence includes objects, documents, fingerprints, photographs of the scene, and the like. Additionally, the evidence may include unknown substances or substances with a suspected identity, where the identity needs to be determined or confirmed. Such substances may be very small in quantity, may be dispersed over a comparatively large area, and may include materials such as: body fluids, hairs, flakes of skin, fibers, drugs, various chemicals, gunpowder residue, flammable materials, tobacco ashes, cosmetics, and the like. Such materials may be collected at a scene and subjected to chemical and/or DNA analysis for identification or for association with a particular individual.

For collecting substance samples, investigators typically use fibrous swabs, such as swabs made of fibers of cotton, cellulose, rayon, polyester, and other types of fibers. Such swabs not only absorb liquids and solids entrained in liquids but also trap dry substances such as particulate materials. The swabs are kept in closed bags or containers prior to use to maintain sterility and are replaced in such containers after use to avoid contamination of the sample gathered. After replacement of a swab in a container, the container is usually marked with a time and date and identity of the investigator and other information to establish a chain of custody of the sample.

Conventional swabs are formed of a "stick" such as a shaft of wood, tubular plastic, or tubular or rolled paper with a pad of cotton or other fiber, sponge material, or other absorbent material attached to the end of the shaft, either mechanically or by an inert adhesive. A problem with conventional swabs is that there is a danger of contamination of the sample if it is necessary to put the swab down, for example, to open a bag or container in which the swab will be placed. Also, if it is necessary to set the swab down to dry, in a propped up condition or extending over the edge of a table, there is a risk of contamination of the sample.

SUMMARY OF THE INVENTION

The device provides an improved low pressure sample collection apparatus for collecting samples of substances and protecting such samples from contamination prior to laboratory analysis. Generally, the sample collection apparatus includes a swab assembly including an elongated shaft, a swab member secured to an end of the shaft, and a cap member connected to an end of the shaft opposite the swab member. The cap member has plug members on opposite sides of a central portion thereof to enable the cap member to be plugged into a container member either with the swab member exposed or with the swab member positioned within and protected from contamination within the container member. The cap member may be provided with one or more bores to allow the influx of drying air into the container with the swab member therein to promote drying of a sample on the swab member. Preferably, the shaft is tubular and the cap member has a nipple on a side opposite from the shaft for connection of a low pressure vacuum source to establish an inflow of air through the swab member to thereby facilitate collection of samples onto and within the swab member.

The shaft may include a push-off barrel positioned between the cap member and the swab member for gripping to push the swab member off the shaft for analysis without contaminating any sample on the swab member. The shaft may further include a drying disk encircling the shaft to prop the swab member off a surface on which the sample collection apparatus is placed to allow the swab member to dry. Because the sample collection apparatus is intended for forensic evidence collection, it is necessary for a chain of custody to be established for any sample collected using the apparatus. For this purpose, the container member and the swab assembly are preferably marked with unique identifying indicia, such as matching barcodes, serial numbers, or the like. Such indicia may be provided by adhesively backed paper labels or by etching into the surfaces of the container member and components of the swab assembly. On the swab assembly, the indicia can be applied on the cap member, the shaft, or the push-off barrel if present.

The sample collection apparatus may include casings positioned on the shaft and including a portion which is positioned in surrounding relation to the swab member to control the flow of air about the swab member during sample collection. In general, the casings are slidably positioned on the shaft using a packing member to slide between a retracted position exposing the swab member, as for drying or removal, and an extended position to shroud the swab member. In one embodiment of a swab casing, the casing has a porous region, formed by fritted glass or the like, which allows some air to flow in toward the swab member from the sides, in addition to air which flows through the end of the casing. In another embodiment of a swab casing, the casing is cylindrically expanded at an outer end to a diameter which is somewhat larger than that of the swab member. Finally, a flared embodiment of a swab casing has a flared end, such as a conically flared end, in the region adjacent the swab member.

Objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring now to the drawing figures, the reference numeral 10 generally designates a low pressure sample collection apparatus. The apparatus 10 generally includes a swab assembly 11 and a container member 12. As will be described below, the swab assembly 11 can be engaged with the container 12 in such a manner as to use the container 12 as a handle or as an enclosure to protect the swab assembly 11.

Figure 1:
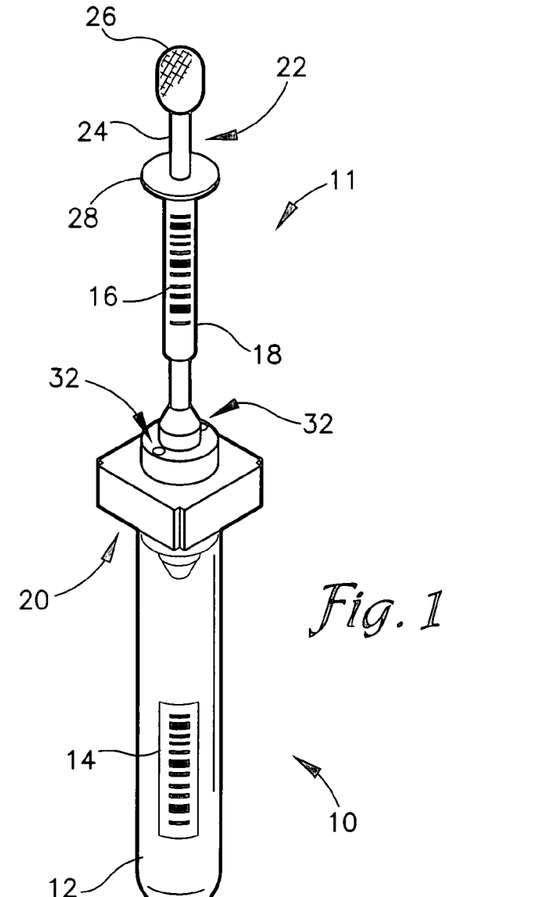
FIG. 1 is a perspective view of an embodiment of a low pressure sample collection apparatus, shown with an embodiment of a container member plugged onto a cap member for use of the container member as a handle.
Figure 1A:
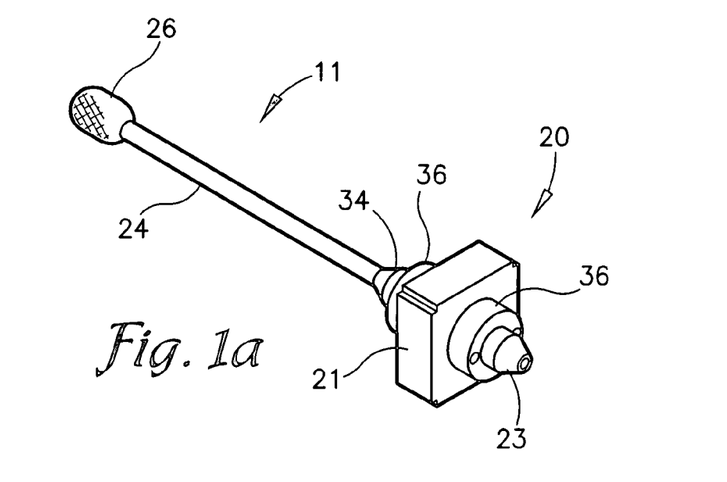
FIG. 1*a* is a perspective view of the sample collection apparatus with the container member removed.
Figure 2A:
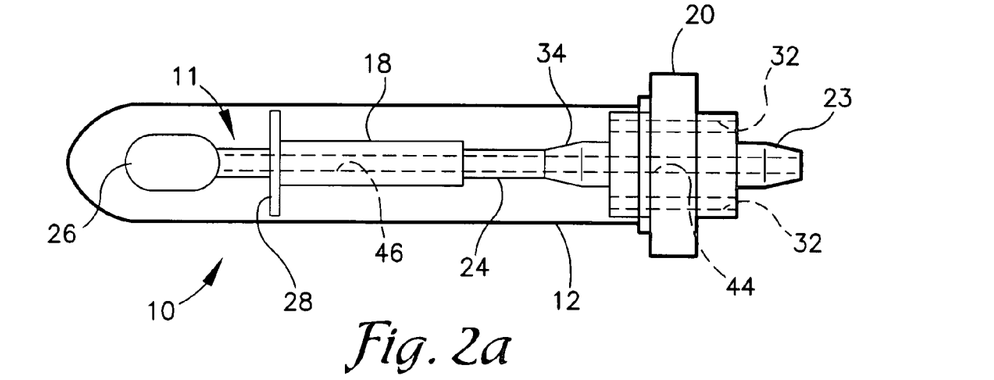
FIG. 2*a* is an enlarged side elevational view of the sample collection apparatus of FIG. 1, showing the container member plugged onto the cap member to enclose a swab member within the container and with push-off barrel and a drying disk adjacent the swab member.
Figure 3:
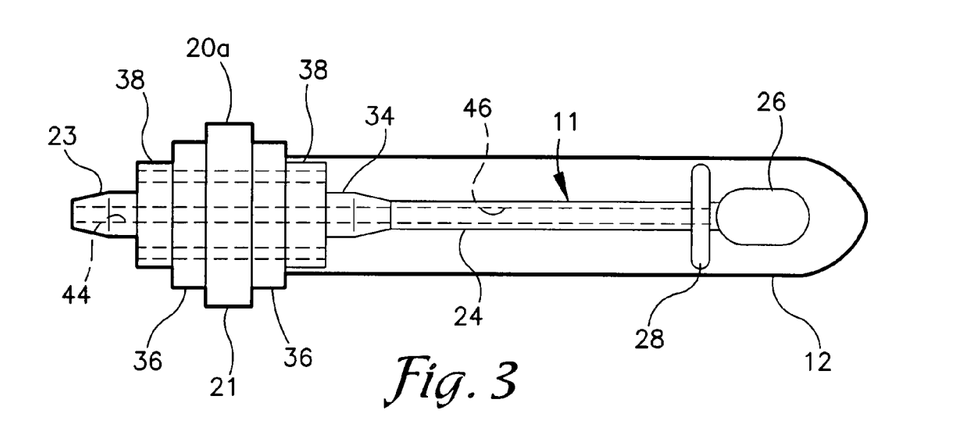
FIG. 3 is an enlarged side elevational view of a modified embodiment of the sample collection apparatus including a cap member having plug members of varying diameters to enable plugging the cap into a variety of sizes of containers or other receptacles.

Referring to FIG. 1, the swab assembly 11 includes a cap member 20 having a tubular shaft 24 extending from one side thereof from a shaft connection portion 34 (FIG. 2). An absorbent or swab member 26 is secured to an outer end of the shaft 24 to form a sample collection head 22. The cap member 20 includes a central cap portion 21 with stopper or plug members 36 extending from opposite sides thereof. One of the plug members 36 has the shaft connection portion 34 extending therefrom. The opposite plug member 36 has a vacuum connection or nipple 23 extending therefrom. The illustrated central cap portion 21 has a square cross section which prevents the swab assembly 11 from rolling if the assembly should be placed on a surface. The plug members 36 have the same diameter so that either plug member 36 can be inserted into the end of the container 12. The illustrated container member 12 has an open mouth at one end and is closed at an opposite end. The cap member 20 may have passages or bores 32 formed through the plug members 36 to enable drying air to enter the container 12 when the collection head 22 is positioned therein, as shown in FIG. 3, to dry the swab member 26. As shown in FIG. 1 two bores 32 are present in a preferred embodiment to assist air circulation into the tube for drying of the specimen on the collection head 22.

Referring to FIG. 1, a push-off barrel 18 is co-axially mounted onto the shaft 24 and is slidable thereon. The barrel 18 can be used to push the swab member 26 off the shaft 24, as for analysis, without touching and possibly contaminating a sample on the swab member 26. Additionally, the swab assembly 11 may be provided with a drying disk 28 encircling the shaft 24. The disk 28 has a diameter sufficient to prevent contact of the swab member 26 with a resting surface if the swab assembly 11 is placed on such a surface to dry. The disk 28 may be of a flat circular construction or of a fatter doughnut-shaped configuration.

In order to establish a chain of custody of any evidence sample taken with the apparatus 10, it is necessary to associate the sample with the investigating officer or an investigating technician and with the scene where the sample was taken. In order to facilitate establishing such a chain of custody, the illustrated apparatus 10 is preferably marked with identifying indicia, such as indicia 14 applied to the container 12 and indicia 16 applied to the swab assembly 11, such as on the barrel 18. Such indicia 14 and 16 may be in the form barcodes, as illustrated, serial numbers, or the like. Preferably, the indicia 14 and 16 are identical so that a swab assembly 11 can be matched with a container 12. Since barcodes are typically read by laser scanning devices, it may be easier to scan the container barcode 14 when the swab assembly 11 is positioned within the container 12. Preferably, each indicia set 14, 16 is unique to a particular sample collection apparatus 10 so that no two apparatus 10 have the same indicia set. This prevents the substitution of evidence for evidence that was originally collected at a scene. Alternatively, other means of marking components of the apparatus 10 for identification are foreseen, such as the provision of tags (not shown) having writable surfaces. Additionally, it is foreseen that some form of tamper seal could be applied to the apparatus 10, such as an adhesive tamper seal (not shown) adhered to the cap member 20 and container 12 after the swab assembly 11 is positioned within the container 12 to show if the cap member 20 has been removed from the container 12. In addition cap member 20, or some portion thereof, may be provided with a color code so that a particular color of cap member 20 is used for the collection of a particular type of evidence specimen. For example a red colored cap member 20 may be used for the collection of a blood evidence sample while a blue cap member 20 may be used for the collection of an evidence sample of unknown material.

Figure 2B:
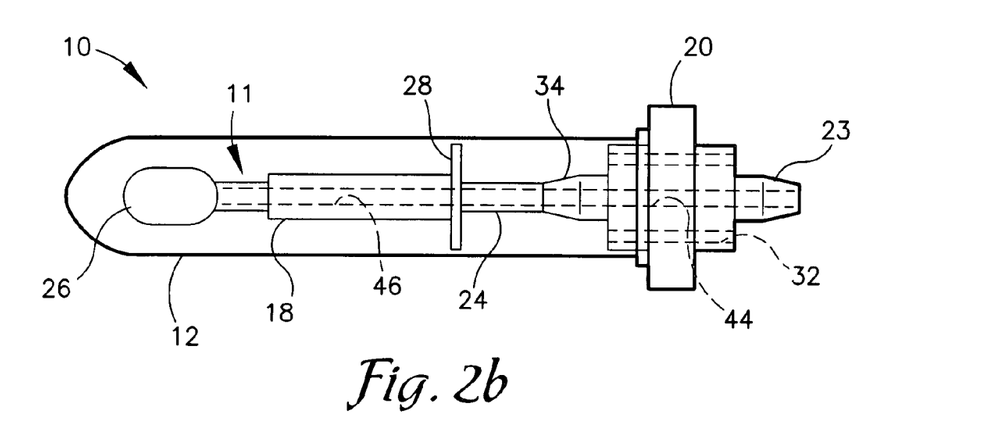
FIG. 2b is a view similar to FIG. 2a and showing the drying disk of the sample collection apparatus positioned adjacent the cap member.

FIG. 1 shows the sample assembly 11 extending from the container member 12 so that the container 12 can be used as a handle to facilitate manipulation of the apparatus 10 to collect a substance sample. FIG. 2a shows the swab assembly 11 positioned within the container 12. In FIG. 2a, the drying disk 28 is positioned between the barrel 18 and the swab member 26. Alternatively, the drying disk 28 could be positioned between the barrel 18 and the connection portion 34 of the cap member 20, as shown in FIG. 2b. The drying disk 28 can also function as a centering disk to prevent the swab member 26 from contacting inner surfaces of the container 12 when positioned therein. As shown in FIGS. 2a and 2b, an airflow passage 46 extends through the shaft 24 and communicates with a passage 44 through the cap member 20, including the connection portion 34 of the cap 20, the plug portions 36, the central cap portion 21, and the nipple 23.

FIG. 3 shows the sample collection apparatus 10 with a modified cap member 20a. The cap member 20a includes a central portion 21 with plug members 36 extending from opposite sides thereof. Additionally, the cap 20a includes a second set of plug members 38 extending from outer surfaces of the plug members 36. As illustrated, the plug members 38 have a smaller diameter than the plug members 36 to enable them to be inserted into containers or other devices, such as laboratory equipment having different diameters. The nipple 23 and shaft connection portion 34 extend from opposite outer surfaces of the plug members 38. The modified cap member 20a includes the passage 44 which communicates with the passage 46 within the shaft 24.

Figure 4:
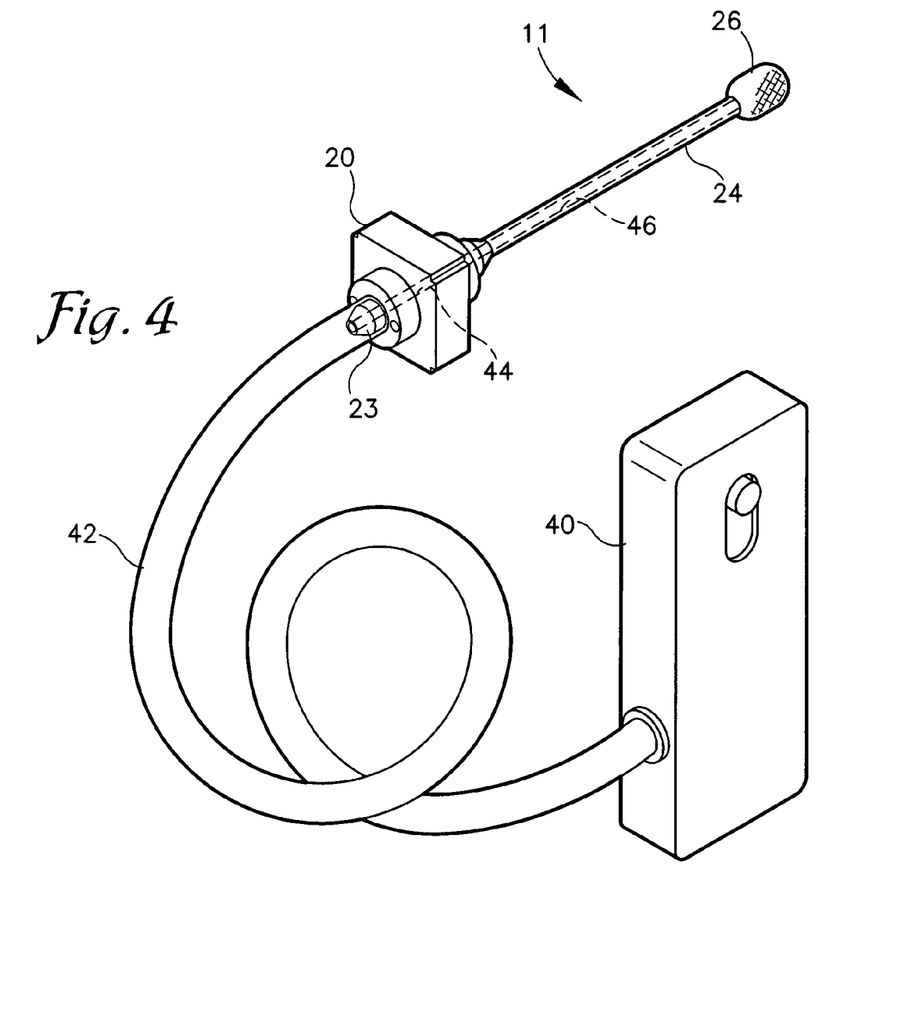
FIG. 4 is a perspective view of the sample collection apparatus, shown with a low pressure vacuum source connected thereto.

Referring now to FIG. 4, an additional aspect is shown which comprises the use of a suction device and method of sample collection. The suction for the sample collection is provided by a portable vacuum device or source 40 which is attached by vacuum hose 42 to the nipple 23 of the cap 20. In this embodiment, a passageway 44 is provided through cap 20. This passage 44 in cap 20 communicates with passage 46 within the shaft 24, which extends to within the swab member 26 The vacuum device 40 is activated to draw air through the swab member 26 to collect particles of a substance within the swab member 26 for later analysis. After collection of a sample, the hose 42 may be disconnected from the nipple 23 and the swab assembly 11 placed within a container 12 to prevent contamination or dilution of the sample. The vacuum device 40 preferably draws air at a relatively low pressure to avoid contaminating the sample with extraneous materials during collection. To further assist in the release of specimen from the swab member 26, the swab 26 may be coated with a dissolvable coating such a albumin or other suitable coating medium. The attracted specimen particles may then be released from the surface of swab member 26 when the dissolvable coating is put into solution.

Figure 5:
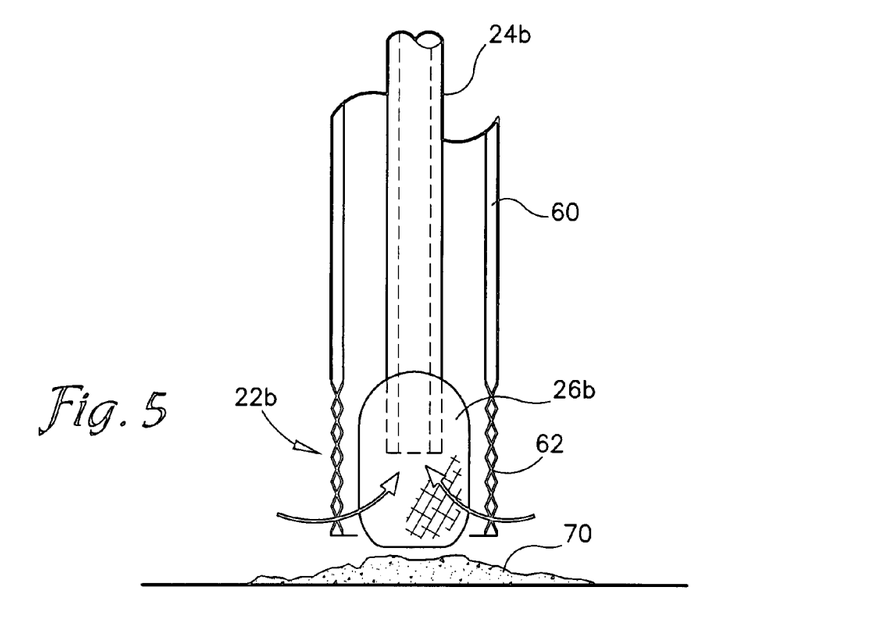
FIG. 5 is an enlarged fragmentary cross-sectional view of a second modified embodiment of the sample collection apparatus which includes a cylindrical swab casing with a porous region in the vicinity of the swab member to control the flow of air about the swab member.
Figure 5A:
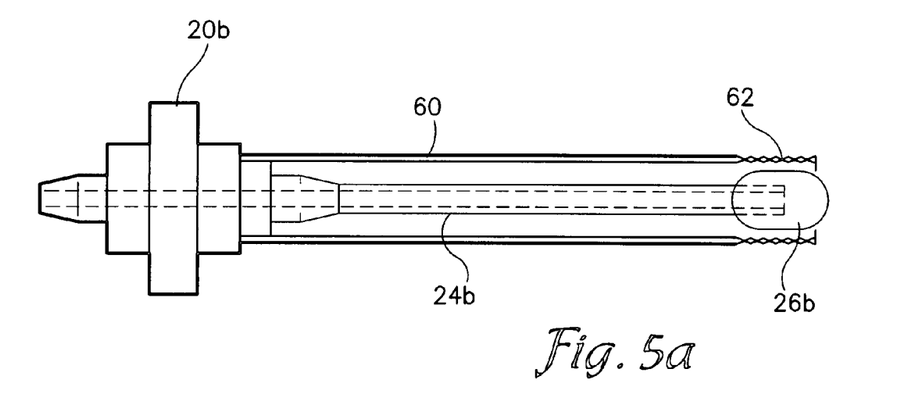
FIG. 5a is a side elevational view of the second modified embodiment of FIG. 5 showing the sample collection apparatus with the casing shown in cross section.

Referring now to FIGS. 5 and 5A an embodiment is shown in which the suction generated by vacuum device 40 travels through cap 20b to provide a reduced pressure atmosphere in a cylindrical casing 60 that coaxially surrounds shaft 24b or collection head 22b. In this manner a low pressure atmosphere, in relation to the general environment outside of casing 60, is provided in casing 60 and to the swab member 26b. Adjacent the swab 26b on casing 60 is a fritted area 62 or an area provided with multiple voids that allow the atmospheric air to enter into casing 60 (FIG. 5). As the air enters voids or fritted area 62 it also draws specimen 70 upwardly onto the swab member 26b. This can be particularly useful where a dried or flaked specimen is located in a cloth or carpet or other woven or porous structure. The casing 60 controls the flow of air about the swab member 26b to focus or confine the area of collection of the specimen 70.

Figures 6, 6A:
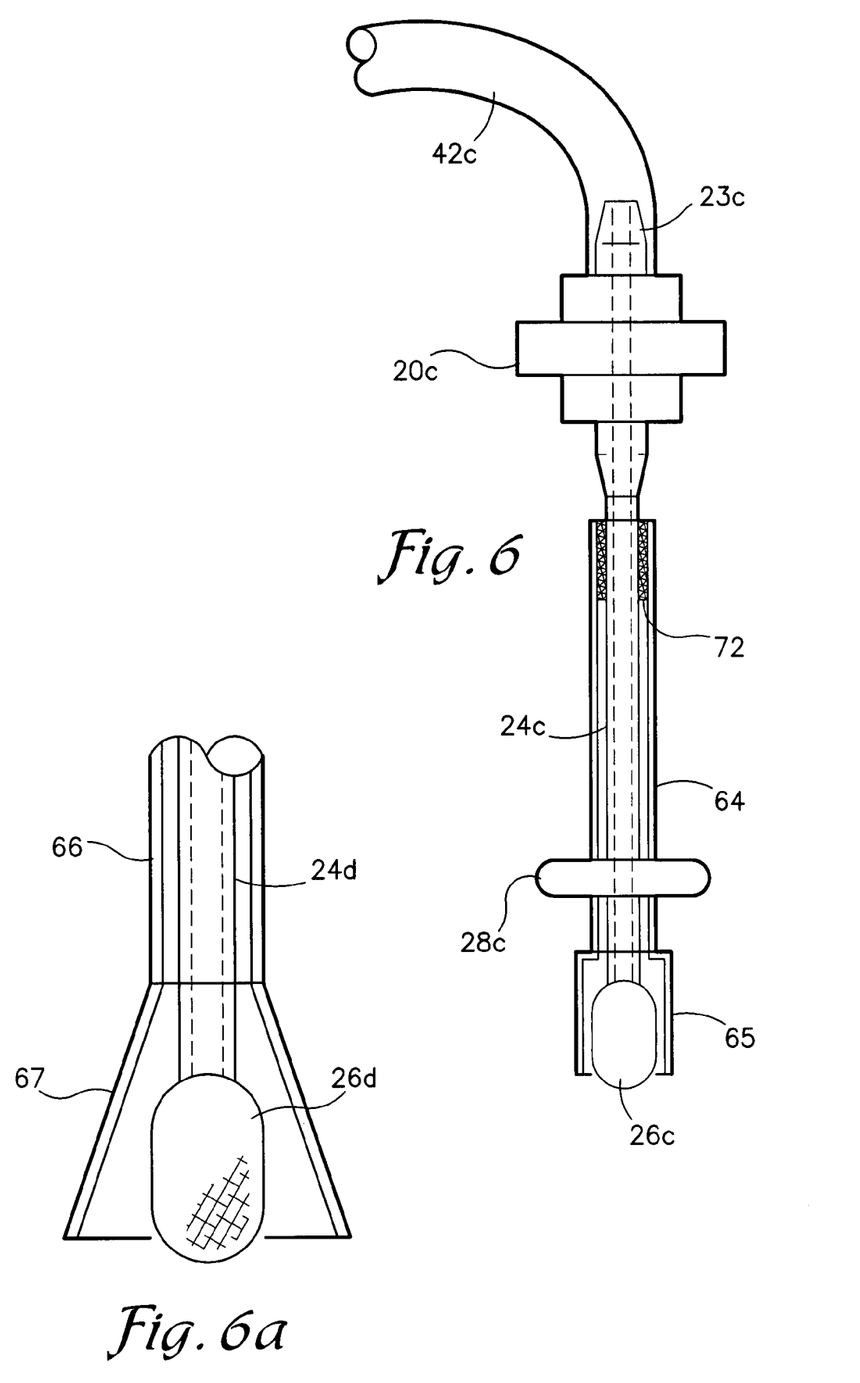
FIG. 6 is a side elevational view of a third modified embodiment of the sample collection apparatus including a slidable swab casing having a cylindrically expanded section adjacent the swab member.
FIG. 6a is an enlarged fragmentary side elevational view a fourth modified embodiment of the sample collection apparatus including a swab casing having a conically expanded section adjacent the swab member.

Referring to FIG. 6, an embodiment is shown in which a casing 64 is provided including a cylindrically expanded region 65 surrounding the swab member 26c, with the remainder of the casing 64 surrounding at least a portion of the shaft 24c. The casing 64 slidably engages the shaft 24c by way of a packing 72, enabling the casing to be slid between a retracted position exposing the swab member 26c and an extended position in which the expanded region 65 surrounds the swab member 26c. Similar to the casing 60, the casing 64 controls the flow of air about the swab member 26c to confine the area of sample collection. The illustrated shaft 24c is connected to a cap member 20c, to which a vacuum hose 42c is connected by way of the nipple 23c. The casing 64 may include a drying or centering disk 28c, to enable propping the assembly up for drying of the swab member 26c.

Referring to FIG. 6a, an embodiment is shown in which a casing 66 surrounds a tubular shaft 24d and includes a flared section 67 surrounding a swab member 26d. The illustrated flared section 67 is frusto-conical; however, the use of other shapes is foreseen. The casing 66 may be made slidable on the shaft 24d in a manner similar to that shown in FIG. 6. The casing 66 is provided for a similar purpose to the casings 60 and 64; namely to control the flow of air about the swab member 26d to thereby control the area of sample collection.

Figure 7:
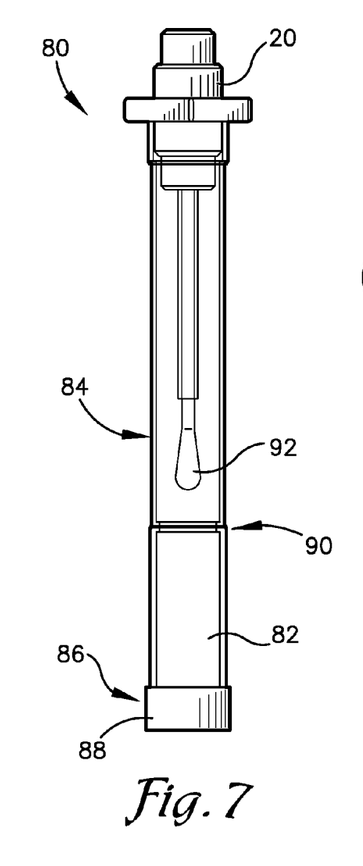
FIG. 7 is a side elevation view of a fifth modified embodiment of the sample collection apparatus having a secondary chamber included in the casing and extending from the portion of the casing containing the swab, the secondary chamber having an openable and closable first end having a cap thereon and the second end of the secondary chamber being in atmospheric communication with the portion of the casing containing the swab.
Figure 8:
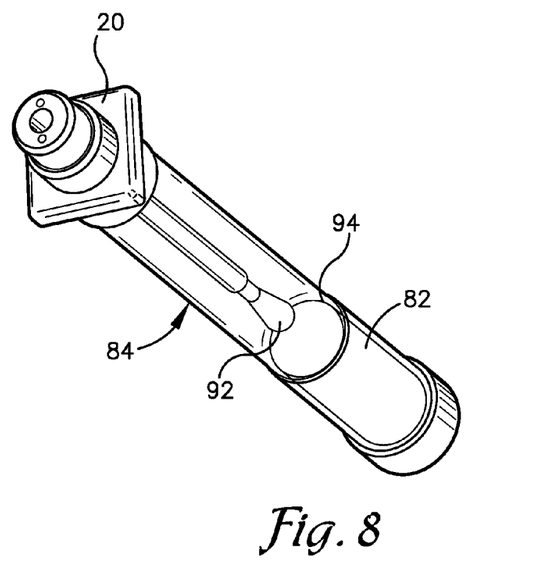
FIG. 8 is a top and side perspective view of the fifth modified embodiment of the sample collection apparatus of FIG. 7.

FIG. 7 is a side elevation view of a fifth modified embodiment 80 of the sample collection apparatus having a secondary chamber 82 included with the casing 84. The secondary chamber 82 extends from the portion of the casing containing the swab. The secondary chamber 82 is provided with an openable and closable first end 86 having a cap 88 thereon. A second end 90 of the secondary chamber 82 is in atmospheric or gaseous communication with the portion of casing 80 containing the swab 92. FIG. 8 shows a top and side perspective view of the embodiment of FIG. 7 and shows shoulder 94 extending inwardly from casing 84. Shoulder 94 operates to restrict the passageway between secondary chamber 82 and the portion of casing 80 containing the swab 92. This restriction allows the placement of materials into secondary chamber 82 so the materials are in atmospheric communication with swab 92, but physical contact with swab 92 is prevented. An alternative structure to shoulder 94 may be a perforated disk or wire mesh or other such porus structure that would allow gaseous or atmospheric communication between secondary chamber 82 and the portion of casing 80 containing the swab 92 while preventing contact with the swab by the material placed in secondary chamber 82.

Figure 9:
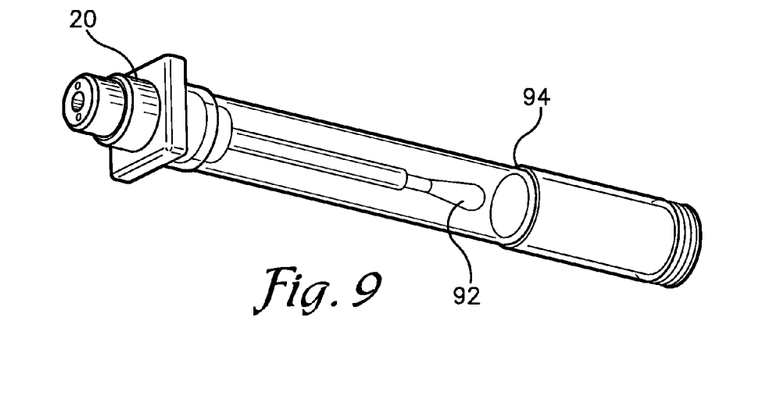
FIG. 9 is a top and side perspective view of the fifth modified embodiment of the sample collection apparatus of FIG. 7 showing the cap removed to permit independent access to the secondary chamber.

FIG. 9 is a top and side perspective view of the embodiment of FIG. 7 and showing cap 88 removed to permit independent access to secondary chamber 82 through first end 86. The independent access permits the introduction or replacement of materials in secondary chamber 82 without disturbing swab 92 and any specimen that may be collected on swab 92. By use of openable and closable first end 86 a material such as a desiccant can be introduced to tube 84 without disturbing swab 92. During use of the sample collection apparatus the desiccant can be replaced through first end 86 as needed without causing disturbance to swab 92. Also, by use of first end 86 to gain access to secondary chamber 82, modifications to the contents of secondary chamber 82 can be made without affecting any tamper evident closure device that has been applied to secure the swab 92 into casing 84.

Figure 10:
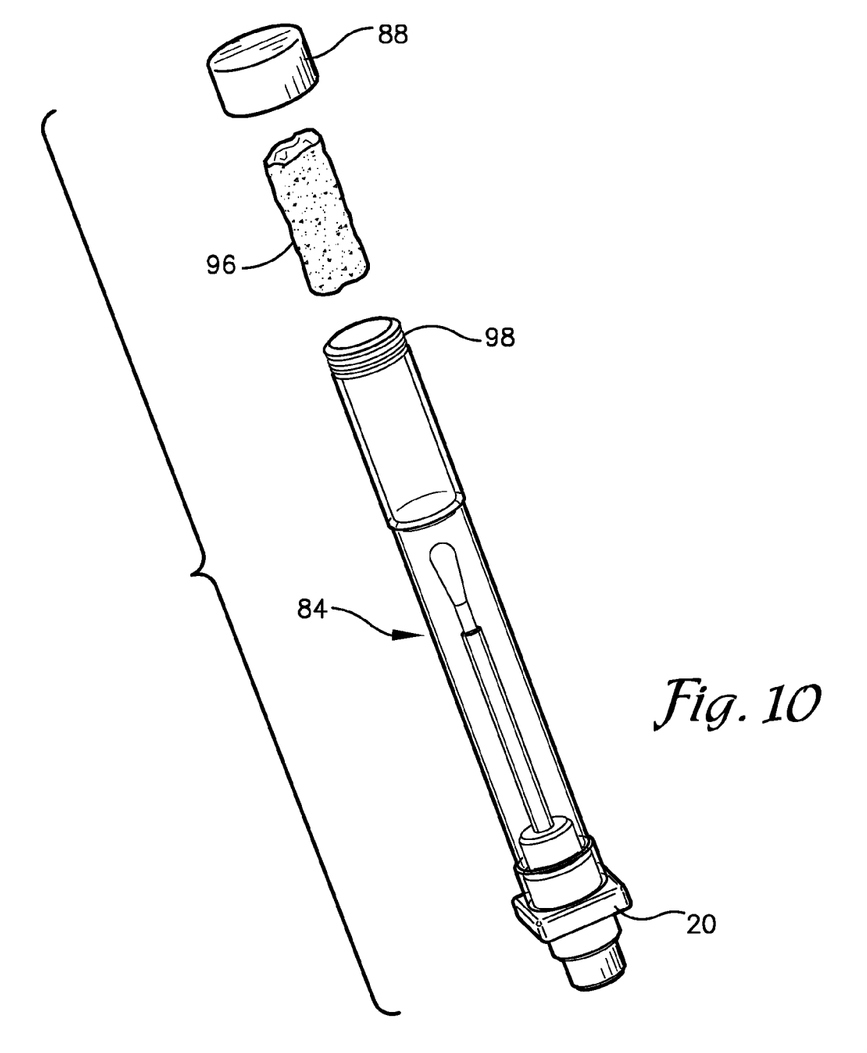
FIG. 10 is a bottom and side partial exploded perspective view of the fifth modified embodiment of the sample collection apparatus of FIG. 7 showing the cap separated from the secondary chamber and a packet of an insert material, such as a desiccant, aligned for insertion into the secondary chamber.

FIG. 10 is a bottom and side partial exploded perspective view of the embodiment of FIGS. 7-9 and showing cap 88 separated from the secondary chamber 82 and a packet 96 of an insert material, such as a desiccant, aligned for insertion into secondary chamber 82. It will be appreciated by those skilled in the art that often it is desirable to have a desiccant or an anti-microbial agent or other such agent proximate to a specimen contained on swab 92. Secondary chamber 82 permits such agents to be introduced into introduced, renewed, and changed out for other agents without disturbance to swab 92 and without damage or disturbance of any chain of custody indicia that may have been applied to cap member 20 (see, FIGS. 1-3). Such chain of custody indicia may be a tape closure or wax seal or other device that would evidence the removal of cap member 20 and such chain of custody indicia are well known in the art. In the present embodiment, cap 88 is removably attached to casing 84 by threads 98, but any will known means of closure may be used to substitute for threads 98.

It is to be understood that while certain forms of the present invention have been illustrated and described herein, it is not to be limited to the specific forms or arrangement of parts described and shown.

I claim:

1. A sample collection apparatus for collecting a sample of a substance and comprising:
   (a) an elongated shaft having opposite shaft ends;
   (b) a swab member removably secured to one of said shaft ends;
   (c) a cap member secured to an end of said shaft opposite said swab member;
   (d) said cap member including a central portion having integrally formed thereon opposite cap surfaces including an inner cap surface and an outer cap surface;
   (e) said inner cap surface having an inner plug member extending therefrom and having said shaft extending from said inner plug member;
   (f) said outer cap surface having an outer plug member extending therefrom,
   (g) said inner plug member and said outer plug member being of a similar size;
   (h) an elongated container member having an open mouth at one end thereof;
   (i) said container member removably receiving said inner plug member therein to position said swab member within said container member to thereby protect said swab member from contamination;
   (j) said container member removably receiving said outer plug member therein to enable use of said container member as a handle to facilitate manipulation of said sample collection apparatus,
   (k) a chamber connected to said container member, said chamber having a first openable and closeable end and said chamber connection to said container member providing gaseous communication between said container member and said chamber.

2. A sample collection apparatus as set forth in claim 1 and including:
   container identification indicia marked on said container member;
   swab identification indicia marked on said shaft; and
   said container identification indicia matching said swab identification indicia.

3. A sample collection apparatus as set forth in claim 2 wherein: (a) said container identification indicia and said swab identification indicia are matching barcodes.

4. A sample collection apparatus as set forth in claim 1 and including: (a) an air bore formed through said cap member to enable entry of drying air into said container member to dry said swab member when said swab member is positioned within said container member.

5. A sample collection apparatus as set forth in claim 1 and including: (a) a push-off barrel positioned in telescoping relation on said shaft between said inner plug member and said swab member, said barrel being selectively pushed into engagement with said swab member to separate said swab member from said shaft.

6. A sample collection apparatus as set forth in claim 1 and including: (a) a drying disk positioned on said shaft in such a manner and having such a diameter as to space said swab member from a surface when said sample collection apparatus is placed on such a surface.

7. A sample collection apparatus as set forth in claim 1 and including: (a) swab identification indicia positioned on said shaft.

8. A sample collection apparatus as set forth in claim 1 wherein: (a) said central portion of said cap member has a non-round cross sectional shape.

9. A sample collection apparatus as set forth in claim 1 wherein said inner plug member and said outer plug member are respectively a first inner plug member and a first outer plug member, each with a first cylindrical diameter, and said cap member includes:
   (a) a second inner plug member extending from said first inner plug member and a second outer plug member extending from said first outer plug member; and
   (b) said second inner and outer plug members have a second cylindrical diameter which is less than said first cylindrical diameter.

10. A sample collection apparatus as set forth in claim 1 and including:
   (a) said shaft being tubular and including a shaft passage communicating with said swab member;
   (b) said cap member having a cap passage communicating with said shaft passage;
   (c) said outer plug member having a nipple extending therefrom, said nipple having a nipple passage communicating with said cap passage; and
   (d) said nipple enabling connection of a vacuum source to said sample collection apparatus to thereby draw air through said swab member to facilitate collecting a sample of a substance.

11. A sample collection apparatus as set forth in claim 10 and including: (a) a cylindrical casing secured to said cap member and extending therefrom to a length adjacent an outer end of said swab member, said casing having a casing diameter slightly greater than a swab diameter of said swab member, said casing controlling flow of air about said swab member.

12. A sample collection apparatus as set forth in claim 10 and including: (a) a cylindrical casing secured to said cap member and extending therefrom to a length adjacent an outer end of said swab member, said casing having a casing diameter slightly greater than a swab diameter of said swab member, said casing including a porous region surrounding at least a portion of said swab member to thereby control flow of air about said swab member.

13. Sample collection apparatus as set forth in claim 10 and including:
   (a) a cylindrical casing secured to said cap member, said casing having an inner end and an opposite outer end;
   (b) said casing having a first cylindrical diameter along said shaft and a second cylindrical diameter at an outer end which is slightly greater than a swab diameter of said swab member to form an expanded region;

(c) said casing including a cylindrical packing within said inner end which sealingly and slidably engages said shaft;

(d) said casing being slidable to a first position with said expanded region surrounding said swab to protect said swab from contact and to control flow of air about said swab member; and (e) said casing being slidable to a second position in which said expanded region is retracted from said swab member to enable drying of said swab member.

14. A sample collection apparatus as set forth in claim 13 and including: (a) a drying disk positioned on said casing in such a manner and having such a diameter as to space said swab member from a surface when said sample collection apparatus is placed on such a surface and said casing is in said second position.

15. A sample collection apparatus as set forth in claim 10 and including:
   (a) a cylindrical casing secured to said cap member, said casing having an inner end and an opposite outer end;
   (b) said casing having a first cylindrical diameter along said shaft from said inner end toward said outer end; and
   (c) said casing having a flared section which is radially spaced from said swab member.

16. A sample collection apparatus as set forth in claim 15 wherein: (a) said flared section has a frusto-conical shape.

17. A sample collection apparatus for collecting a sample of a substance and comprising:
   (a) an elongated shaft having opposite shaft ends;
   (b) a swab member removably secured to one of said shaft ends;
   (c) a cap member secured to an end of said shaft opposite said swab member;
   (d) said cap member including a central portion having integrally formed thereon with opposite cap surfaces including an inner cap surface and an outer cap surface;
   (e) said inner cap surface having an inner plug member extending therefrom and having said shaft extending from said inner plug member;
   (f) said outer cap surface having an outer plug member extending therefrom;
   (g) said inner plug member and said outer plug member being of a similar size;
   (h) an elongated container member having an open mouth at one end thereof and being closed at an end opposite said mouth;
   (i) said container member removably receiving said inner plug member therein to position said swab member within said container member to thereby protect said swab member from contamination;
   (j) said container member removably receiving said outer plug member therein to enable use of said container member as a handle to facilitate manipulation of said sample collection apparatus;
   (k) container identification indicia marked on said container member, swab identification indicia marked on said shaft, and said container identification indicia matching said swab identification indicia;
   (l) said shaft being tubular and including a shaft passage communicating with said swab member, said cap member having a cap passage communicating with said shaft passage, said outer plug member having a nipple extending therefrom, said nipple having a nipple passage communicating with said cap passage;
   (m) said nipple enabling connection of a vacuum source to said sample collection apparatus to thereby draw air through said swab member to facilitate collecting a sample of a substance; and,
   (n) a chamber connected to said container member, said chamber having a first openable and closeable end and said chamber connection to said container member providing gaseous communication between said container member and said chamber.

18. A sample collection apparatus as set forth in claim 17 wherein: (a) said container identification indicia and said swab identification indicia are matching barcodes.

19. A sample collection apparatus as set forth in claim 17 and including: (a) an air bore formed through said cap member to enable entry of drying air into said container member to dry said swab member when said swab member is positioned within said container member.

20. A sample collection apparatus as set forth in claim 17 and including: (a) a push-off barrel positioned in telescoping relation on said shaft between said inner plug member and said swab member, said barrel being selectively pushed into engagement with said swab member to separate said swab member from said shaft.

21. A sample collection apparatus as set forth in claim 17 and including: (a) a drying disk positioned on said shaft in such a manner and having such a diameter as to space said swab member from a surface when said sample collection apparatus is placed on such a surface.

22. A sample collection apparatus as set forth in claim 17 wherein: (a) said central portion of said cap member has a non-round cross sectional shape.

23. A sample collection apparatus as set forth in claim 17 wherein said inner plug member and said outer plug member are respectively a first inner plug member and a first outer plug member, each with a first cylindrical diameter, and said cap member includes:
   (a) a second inner plug member extending from said first inner plug member and a second outer plug member extending from said first outer plug member; and
   (b) said second inner and outer plug members have a second cylindrical diameter which is less than said first cylindrical diameter.

24. A sample collection apparatus as set forth in claim 1 further comprising a sample retainer permitting gaseous communication between said chamber second end and said container member said retainer restricting movement of material from said chamber into said container member.

25. A sample collection apparatus as set forth in claim 17 further comprising a sample retainer permitting gaseous communication between said chamber second end and said container member said retainer restricting movement of material from said chamber into said container member.

* * * * *